(12) United States Patent
Yu et al.

(10) Patent No.: US 8,088,738 B2
(45) Date of Patent: Jan. 3, 2012

(54) THERMOSTABLE ALPHA1-ANTITRYPSIN MUTEIN WITH A DISULFIDE BOND AND THE METHOD FOR PREPARING IT

(75) Inventors: Myeong-Hee Yu, Seoul (KR); Je-Hyun Baek, Gwacheon-si (KR); Cheolju Lee, Seoul (KR)

(73) Assignee: Korea Institute of Science and Technology, Seoul (KR)

( * ) Notice: Subject to any disclaimer, the term of this patent is extended or adjusted under 35 U.S.C. 154(b) by 0 days.

(21) Appl. No.: 12/743,920

(22) PCT Filed: Nov. 22, 2007

(86) PCT No.: PCT/KR2007/005910
§ 371 (c)(1),
(2), (4) Date: May 20, 2010

(87) PCT Pub. No.: WO2009/066807
PCT Pub. Date: May 28, 2009

(65) Prior Publication Data
US 2010/0248309 A1    Sep. 30, 2010

(30) Foreign Application Priority Data
Nov. 21, 2007  (KR) .................. 10-2007-0118936

(51) Int. Cl.
*A61K 38/55* (2006.01)
*C07K 14/00* (2006.01)
(52) U.S. Cl. ...................................... 514/20.3; 530/350
(58) Field of Classification Search .................. None
See application file for complete search history.

(56) References Cited

U.S. PATENT DOCUMENTS

| 4,711,848 | A   | 12/1987 | Insley et al. |
| 4,732,973 | A   | 3/1988  | Barr et al. |
| 6,562,799 | B1* | 5/2003  | Semenza ............... 514/44 R |
| 6,833,262 | B1  | 12/2004 | Travis et al. |

FOREIGN PATENT DOCUMENTS

| EP | 0137633 | 4/1985 |
| KR | 19930012114 | 12/1993 |
| KR | 0133252 | 12/1997 |
| WO | WO 94/26781 | 11/1994 |

OTHER PUBLICATIONS

Definition of "represent", obtained from merriam-webster.com, last viewed on Feb. 18, 2011, 1 page.*
Definition of "mutein", obtained from medical-dictionary.thefreedictionary.com/mutein last viewed on Feb. 17, 2011, 1 page.*
Definition of "mutein", obtained from mondofacto.com/facts/dictionary?mutein, last viewed on Feb. 17, 2011, 1 page.*
Kolarich et al., Proteomics 6:3369-3380, 2006.*
Hopkins et al., J. Biol. Chem. 272:3905-3909, 1997.*
Veldkamp et al., Protein Expression and Purification 52:202-209, Mar. 2007.*
Baek et al., "Probing the local conformational change of alpha 1-antitrypsin," *Protein Sci.*, vol. 16, No. 9, pp. 1842-1850, 2007.
Beatty et al., "Kinetics of association of serine proteinases with native and oxidized alpha-1-proteinase inhibitor and alpha-1-antichymotrypsin," *J. Biol. Chem.*, vol. 255, No. 9, pp. 3931-3934, 1980.
Bollen et al., "Expression of human alpha 1-antitrypsin in *Escherichia coli*," *FEBS Lett.*, vol. 166, No. 1, pp. 67-70, 1984.
Cabezon et al., "Expression of human alpha 1-antitrypsin cDNA in the yeast *Saccharomyces cerevisiae*," *Proc. Natl. Acad. Sci. USA*, vol. 81, pp. 6594-6598, 1984.
Carrell, "Reactive-centre variants of alpha 1-antitrypsin. A new range of anti-inflammatory agents," *Biotechnology and Genetic Engineering Reviews*, vol. 4, pp. 291-309, 1986.
Carrell et al., "The Molecular Pathology of the Serpins," *Mol. Biol. Med.*, vol. 6, pp. 35-42, 1989.
Courtney et al., "High-level production of biologically active human alpha 1-antitrypsin in *Escherichia coli*," *Proc. Natl. Acad. Sci. USA*, vol. 81, pp. 669-673, 1984.
Courtney et al., "Synthesis in *E. coli* of alpha 1-antitrypsin variants of therapeutic potential for emphysema and thrombosis," *Nature*, vol. 313, pp. 149-151, 1985.
Engh et al., "The S variant of human alpha 1-antitrypsin, structure and implications for function and metabolism," *Protein Eng.*, vol. 2, No. 6, pp. 407-415, 1989.
Hayes, "Genetic diversity of the alpha-1-antitrypsin gene in Africans identified using a novel genotyping assay," *Human Mutation*, vol. 22, No. 1, pp. 59-66, 2003.
Huber and Carrell, "Implications of the three-dimensional structure of alpha 1-antitrypsin for structure and Function of Serpins," *Biochemistry*, vol. 28, No. 23, pp. 8951-8971, 1989.
Im et al., "Metastability in the inhibitory mechanism of human alpha 1-antitrypsin," *J. Biol. Chem.*, vol. 274, No. 16, pp. 11072-11077, 1999.
Ito et al., "Transformation of intact yeast cells treated with alkali cations," *J. Bacteriol.*, vol. 153, No. 1, pp. 163-168, 1983.
Johansen et al., "High-level production of fully active human alpha 1-antitrypsin in *Escherichia coli*," *Mol. Biol. Med.*, vol. 4, pp. 291-305, 1987.
Kim et al., "Cloning and Expression of Human α1—antitrypsin cDNA in yeast *Saccharomyces cerevisiae*," *Korean Biochem. J.*, vol. 23, No. 2, pp. 263-268, 1990.
Kim et al., "Expression and Secretion of Heterologous Protein in Yeast," *Korean Journal of Microbiology*, vol. 30, No. 2, pp. 108-112, 1992.

(Continued)

Primary Examiner — David J Steadman
(74) Attorney, Agent, or Firm — Ladas & Parry LLP

(57) ABSTRACT

The present invention relates to a thermostable alpha-1-antitrypsin mutein with a disulfide bond and a preparation method of the same, more precisely an alpha-1-antitrypsin mutein with improved thermostability, compared with the conventional thermostable alpha-1-antitrypsin mutein (Korean Patent No. 133252), resulted from the process of substituting the 168th and 189th amino acids of the alpha-1-antitrypsin with cysteines which are then linked by a disulfide bond, with keeping its alpha-1-antitrypsin activity unchanged, and a preparing method of the same. The thermostable alpha-1-antitrypsin mutein with a disulfide bond of the invention can be effectively used for a protein based therapeutic agent which is very stable in vivo, and can be applied further in various fields including in the development of a diagnostic reagent and in the preparation of an affinity column.

15 Claims, 4 Drawing Sheets

OTHER PUBLICATIONS

Kunkel et al., "Rapid and efficient site-specific mutagenesis without phenotypic selection," *Methods in enzymol.*, vol. 154, No. 19, pp. 367-382, 1987.

Lee and Yu, "Isolation of Human α 1—antitrypsin cDNA and its expression in *E . Coli.,*" *Korean Biochem. J.*, vol. 22, No. 2, p. 148-153, 1989 (KOREAN).

Lee et al., "Molecular Properties of Recombinant Human α1-antitrypsin Produced in *Escherichia coli* and in vitro Translation System," *Molecules and Cells*, vol. 3, pp. 71-74, 1993.

Lee et al., "Characterization of a human alpha 1-antitrypsin variant that is as stable as ovalbumin," *J. Biol. Chem.*, vol. 273, No. 5, pp. 2509-2516, 1998.

Lomas et al., "The mechanism of Z alpha 1-antitrypsin accumulation in the liver," *Nature*, vol. 357, pp. 605-607, 1992.

Lomas et al., "Effect of the Z mutation on the physical and inhibitory properties of alpha 1-antitrypsin," *Biochemistry*, vol. 32, pp. 500-508, 1993.

Long et al., "Complete sequence of the cDNA for human alpha 1-antitrypsin and the gene for the S variant," *Biochemistry*, vol. 23, pp. 4828-4837, 1984.

Pace, "Measuring and increasing protein stability," *Trends in Biotechnology*, vol. 8, pp. 93-98, 1990.

Rosenberg et al., "Synthesis in yeast of a functional oxidation-resistant mutant of human alpha-1-antitrypsin," *Nature*, vol. 312, pp. 77-80, 1984.

Shin et al., "Viscous drag as the source of active site perturbation during protease translocation: insights into how inhibitory processes are controlled by serpin metastability," *J. Mol. Biol.*, vol. 359, No. 2, pp. 378-389, 2006.

Shin et al., "Misfolding-assisted selection of stable protein variants using phage displays," *J. Biochem. Mol. Biol.*, vol. 39, No. 1, pp. 55-60, 2006.

Sidhar et al., "Mutations which impede loop/sheet polymerization enhance the secretion of human alpha 1-antitrypsin deficiency variants," *J. Biol. Chem.*, vol. 270, No. 15, pp. 8393-8396, 1995.

Studier and Moffatt, "Use of bacteriophage T7 RNA polymerase to direct selective high-level expression of cloned genes," *J. Mol. Biol*, vol. 189, pp. 113-130 1986.

Sutiphong et al., "Selection of mutations that increase alpha 1-antitrypsin gene expression in *Escherichia coli*," *Mol. Biol. Med.*, vol. 4, pp. 307-322, 1987.

Tessier et al., "RNA structural elements for expression in *Escherichia coli*. Alpha 1-antitrypsin synthesis using translation control elements based on the cII ribosome-binding site of phage lambda," *FEBS Lett.*, vol. 208, No. 2, pp. 183-188, 1986.

Travis et al., "Isolation and properties of recombinant DNA produced variants of human alpha 1-proteinase inhibitor," *J. Biol. Chem.*, vol. 260, No. 7, p. 4384-4389, 1985.

Yi et al., "Structural factors affecting the choice between latency transition and polymerization in inhibitory serpins," *Protein Sci.*, vol. 16, No. 5, pp. 833-841, 2007.

\* cited by examiner

FIG 1

```
  1  Glu Asp Pro Gln Gly Asp Ala Ala Gln Lys Thr Asp Thr Ser His   15
 16  His Asp Gln Asp His Pro Thr Phe Asn Lys Ile Thr Pro Asn Leu   30
 31  Ala Glu Phe Ala Phe Ser Leu Tyr Arg Gln Leu Ala His Gln Ser   45
 46  Asn Ser Thr Asn Ile Phe Phe Ser Pro Val Ser Ile Ala Thr Ala   60
 61  Phe Ala Met Leu Ser Leu Gly Thr Lys Ala Asp Thr His Asp Glu   75
 76  Ile Leu Glu Gly Leu Asn Phe Asn Leu Thr Glu Ile Pro Glu Ala   90
 91  Gln Ile His Glu Gly Phe Gln Glu Leu Leu Arg Thr Leu Asn Gln  105
106  Pro Asp Ser Gln Leu Gln Leu Thr Thr Gly Asn Gly Leu Phe Leu  120
121  Ser Glu Gly Leu Lys Leu Val Asp Lys Phe Leu Glu Asp Val Lys  135
136  Lys Leu Tyr His Ser Glu Ala Phe Thr Val Asn Phe Gly Asp Thr  150
151  Glu Glu Ala Lys Lys Gln Ile Asn Asp Tyr Val Glu Lys Gly Thr  165
166  Gln Gly Lys Ile Val Asp Leu Val Lys Glu Leu Asp Arg Asp Thr  180
181  Val Phe Ala Leu Val Asn Tyr Ile Phe Phe Lys Gly Lys Trp Glu  195
196  Arg Pro Phe Glu Val Lys Asp Thr Glu Glu Glu Asp Phe His Val  210
211  Asp Gln Val Thr Thr Val Lys Val Pro Met Met Lys Arg Leu Gly  225
226  Met Phe Asn Ile Gln His Cys Lys Lys Leu Ser Ser Trp Val Leu  240
241  Leu Met Lys Tyr Leu Gly Asn Ala Thr Ala Ile Phe Phe Leu Pro  255
256  Asp Glu Gly Lys Leu Gln His Leu Glu Asn Glu Leu Thr His Asp  270
271  Ile Ile Thr Lys Phe Leu Glu Asn Glu Asp Arg Arg Ser Ala Ser  285
286  Leu His Leu Pro Lys Leu Ser Ile Thr Gly Thr Tyr Asp Leu Lys  300
301  Ser Val Leu Gly Gln Leu Gly Ile Thr Lys Val Phe Ser Asn Gly  315
316  Ala Asp Leu Ser Gly Val Thr Glu Glu Ala Pro Leu Lys Leu Ser  330
331  Lys Ala Val His Lys Ala Val Leu Thr Ile Asp Glu Lys Gly Thr  345
346  Glu Ala Ala Gly Ala Met Phe Leu Glu Ala Ile Pro Met Ser Ile  360
361  Pro Pro Glu Val Lys Phe Asn Lys Pro Phe Val Phe Leu Met Ile  375
376  Glu Gln Asn Thr Lys Ser Pro Leu Phe Met Gly Lys Val Val Asn  390
391  Pro Thr Gln Lys  (SEQ ID NO: 1)
```

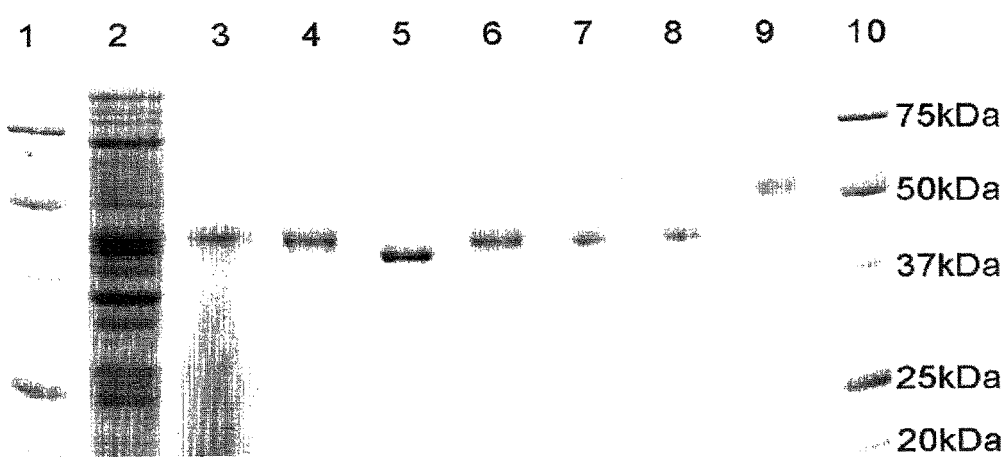

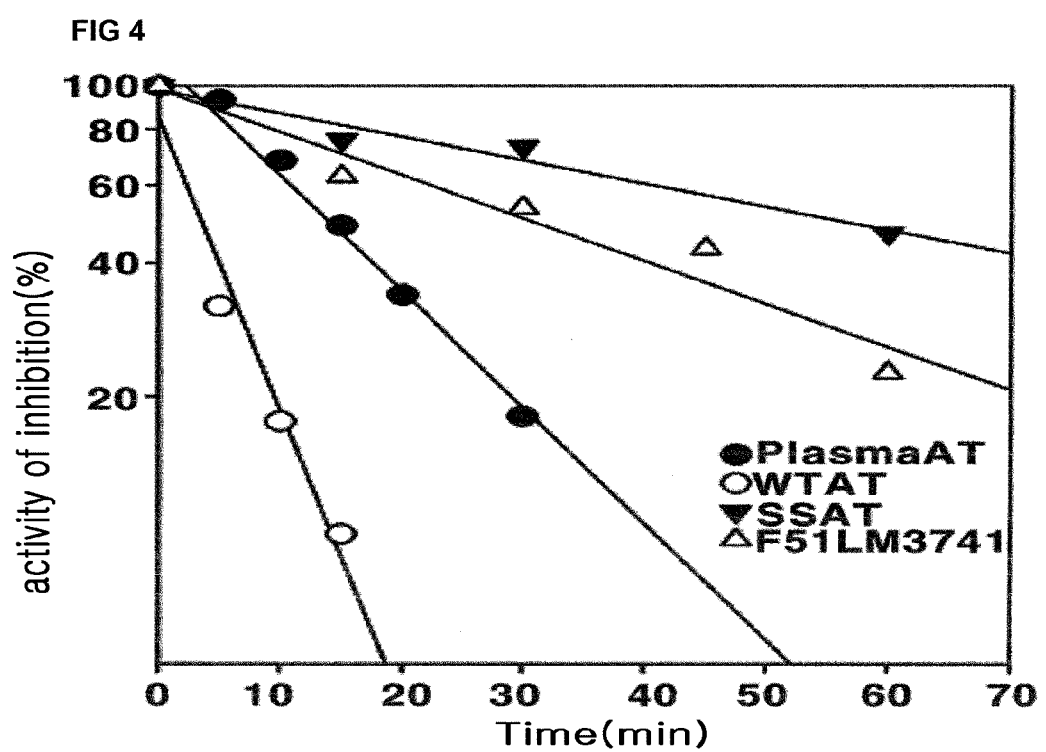

US 8,088,738 B2

THERMOSTABLE ALPHA1-ANTITRYPSIN MUTEIN WITH A DISULFIDE BOND AND THE METHOD FOR PREPARING IT

CROSS REFERENCE TO RELATED APPLICATIONS

This is the §371 U.S. National Stage of International Application No. PCT/KR2007/005910, filed Nov. 22, 2007, which was published in English under PCT Article 21(2), which in turn claims the benefit of Korean Application No. 10-2007-0118936, filed Nov. 21, 2007, which is incorporated herein in its entirety.

TECHNICAL FIELD

The present invention relates to a thermostable alpha-1-antitrypsin mutein with a disulfide bond and a preparation method of the same, more precisely an alpha-1-antitrypsin mutein with improved thermostability, compared with the conventional thermostable alpha-1-antitrypsin mutein (Korean Patent No. 133252), resulted from the process of substituting the $168^{th}$ and $189^{th}$ amino acids of the alpha-1-antitrypsin (referred as 'AT' hereinafter) with cysteines which are then linked by a disulfide bond, with keeping its alpha-1-antitrypsin activity unchanged, and a preparing method of the same.

BACKGROUND ART

The stability has to be maintained in a substance to keep the substance normally functioning. In particular, the stability is a key factor determining shelf life and half life in vivo especially in a substance composed of proteins that are easily denaturated. Thus, to develop a therapeutic agent or diagnostic reagent comprising proteins, it is necessary to improve the stability of candidate compositions for those agents. Protein is weak in keeping its natural form and thus easily inactivated and changed in structure by heat or a chemical denaturant. In the case of the serine based protease inhibitor including antitrypsin, antichymotrypsin and alpha-1-antitrypsin, a polymer is formed in between molecules by heat treatment, resulting in the inactive form.

The conventional therapeutic agent comprising proteins separated and purified from human blood might have problems of limitation of supply and potential contamination with infectious materials such as AIDS or hepatitis virus. Therefore, other attempts have been made to produce a protein therapeutic agent by genetic engineering techniques. However, the recombinant proteins prepared by genetic engineering technique have lower stability than the conventional protein therapeutic agent comprising the proteins separated from human blood. Besides, when the recombinant protein is administered into blood plasma, half-life of the protein decreases rapidly, putting the usability of such recombinant protein as a therapeutic agent in doubt. Attempts have been made to overcome the problem of the lower stability. One of the attempts is the genetic engineering method to produce a mutated protein with improved stability without changing its activity by substituting amino acids via gene mutation. Heat-resistance of a protein is closely associated with stability against degeneration of a protein (Pace, Trends in Biotechnology, 8, 93-98, 1990).

AT is synthesized in liver cells and then secreted into blood. Along with most serine based protease inhibitors existing in blood plasma including trypsin, chymotrypsin, elastase, collagenase, thrombin and plasmin, AT belongs to serpin family. AT is a glycoprotein of 52 kD in molecular weight and is physiologically functioning as an inhibitor to elastase of neutrophiles. In particular, AT prevents elastic fiber from being decomposed by elastase of neutrophiles.

Many cases of innate genetic mutation that causes AT-related pathological symptoms have been reported (Carrell et al., Mol. Biol. Med. 6, 35-42, 1982). In most cases, the decrease of AT level in blood plasma breaks the balance between protease and its inhibitor and therefore the lungs lose flexibility, which develops into emphysema (Gadek and Crystal, in Metabolic Basis of Inherited Disease. Stanbury et al., Eds., McGraw-Hill, New York. pp. 1450-1467).

In addition to the emphysema caused by genetic defection, heavy smoking or serious environmental pollution causes inactivation of protease inhibitor to cause emphysema. To overcome this disease largely found in Caucasian of Northern America and Europe, AT market of at least 100 million dollars/year has been formed and AT extracted from blood has been actually administered as a therapeutic agent.

AT can also be used for the treatment of acute shock syndrome (Robin W. Carrell, Biotechnology and Genetic Engineering Reviews. 4, 291-297 (1986)). Shock syndrome is caused by unbalance between sulfin and protease in blood plasma resulted from the sudden mass-release of neutrophiles. Considering limitation of obtaining the raw material and possible virus infection, preparation methods by genetic engineering techniques have been tried as an alternative.

The nucleotide sequence of DNA encoding AT protein has been already identified (Long et al., Biochemistry 23, 4828 (1984)) and AT gene was expressed in *E. coli* (Bollen et al., FEBS Lett. 16, 67 (1984); Courtney et al., Proc. Natl. Acad. Sci. USA 81. 669 (1984); Tessier et al., FEBS Lett. 208, 183 (1986); Johnsen et al., Mol. Biol. Med. 4, 291 (1987); Sutiphong et al., Mol. Biol. Med. 4, 307 (1987); Lee and Yu, Journal of Biochemistry and Molecular Biology 22, 148 (1989); Lee et al., Molecules and Cells 3, 71-74 (1993)) or yeast (Travis et al., J. Biol. Chem. 260. 4384 (1985); Rosenberg et al., Nature 312, 77 (1984); Cabezon et al., Proc. Natl. Acad. Sci. USA 81, 6594 (1984); Kim et al., Journal of Biochemistry and Molecular Biology 23, 236 (1990); Kim et al., Korean Journal of Microbiology 30, 108 (1992)) according to previous reports.

There was a successful attempt, in which AT activation site, the $358^{th}$ methionine residue was substituted with another amino acid residue by site specific mutagenesis to develop an inhibitor to serine based protease other than elastase or to develop an inhibitor with improved resistance against oxidation (Rosenberg et al., Nature 312, 77-80 (1984); Courtney et al., Nature 313, 149-151 (1985); Barr et al., U.S. Pat. No. 4,732,973; Insley et al., U.S. Pat. No. 4,711,848). The non-glycosylated AT produced in yeast exhibited reduced heat-resistance in vitro and the decrease of heat-resistance was allegedly closely related to the decrease of its half-life in vivo (Travis et al., J. Biol. Chem., 260. 4384 (1985)).

The co-relation between AT structure and AT functions was explained well by Huber and Carrell (Biochemistry 28, 8951-8963 (1989)).

The present inventors continued to study to overcome the problem of instability of AT prepared by genetic engineering techniques. As a result, the present inventors completed this invention by confirming that the $168^{th}$ and the $189^{th}$ amino acid residues of AT were substituted with cysteines and the protein was oxidized, resulting in recombinant mutein AT with a disulfide bond, which had much more improved heat-resistance and thermodynamic stability, compared with the wild type recombinant AT or the patent granted F51L/M374I mutein (Korean Patent No. 133252).

DISCLOSURE

The Sequence Listing is submitted as an ASCII text file in the form of the file named Sequence_Listing.txt, which was created on May 13, 2010, and is 35,304 bytes, which is incorporated by reference herein.

Technical Problem

It is an object of the present invention to provide a thermostable alpha-1-antitrypsin mutein with a disulfide bond and a preparing method of the same.

Technical Solution

To achieve the above object, the present invention provides a human alpha-1-antitrypsin mutein, in which the $168^{th}$ and the $189^{th}$ amino acid residues are substituted with cysteines and oxidized to form an intramolecular disulfide bond and the rest of the sequence is same as the amino acid sequence of a wild type mutein.

The present invention also provides a polynucleotide encoding the alpha-1-antitrypsin mutein.

The present invention further provides an expression vector comprising the polynucleotide encoding the alpha-1-antitrypsin mutein.

In addition, the present invention provides a host cell transformed with the expression vector.

The present invention also provides a preparing method of the thermostable AT mutein comprising the following steps:
1) culturing host cells containing the target expression vector under the optimum growth conditions;
2) separating AT mutein produced from the culture solution;
3) oxidizing AT mutein on the column; and
4) obtaining the thermostable AT mutein with a disulfide bond.

Hereinafter, the present invention is described in detail.

The present invention provides a human alpha-1-antitrypsin mutein (referred as 'AT mutein' hereinafter), in which the $168^{th}$ and the $189^{th}$ amino acid residues are substituted with cysteines and oxidized to form an intramolecular disulfide bond and the rest of the sequence is same as the amino acid sequence of a wild type mutein.

The thermostable AT mutein of the present invention is a recombinant AT produced by substituting the $168^{th}$ amino acid lysine and the $189^{th}$ amino acid phenylalanine of the wild type AT with cysteines which were oxidized to form an intramolecular disulfide bond. And to avoid any unwanted effect from oxidation of the recombinant AT, the $232^{nd}$ cysteine is substituted with serine.

The thermostable AT mutein of the present invention preferably includes the amino acid sequences represented by SEQ. ID. NO: 12 in which the $168^{th}$ and the $189^{th}$ amino acids are substituted with cysteines and SEQ. ID. NO: 13 in which the $232^{nd}$ amino acid is additionally substituted with serine in addition to the above two cysteine substitutions and can also include another sequence originated from human alpha-1-antitrypsin amino acid comprising either the wild type or mutant form of alpha-1-antitrypsin sequence in which the $168^{th}$ and the $189^{th}$ amino acids are substituted with cysteines and those cysteines are oxidized to form an intramolecular disulfide bond.

The amino acid sequence of the recombinant AT of the invention is same as that of the wild type except the two substituted sites (see FIG. 1), and the wild type includes one or more amino acid variations shown in below, in addition to the amino acid sequence of FIG. 1 (SEQ. ID. NO: 1):

$Arg^{101} \rightarrow His^{101}$, $Glu^{204} \rightarrow Lys^{204}$, $Val^{213} \rightarrow Ala^{213}$, $Arg^{223} \rightarrow Cys^{223}$, $Asp^{341} \rightarrow Asn^{341}$, $Glu^{363} \rightarrow Lys^{363}$, $Glu^{376} \rightarrow Asn^{376}$.

The sequences represented by SEQ. ID. NO: 2-NO: 8 are the examples of the above amino acid substitution. Any of these amino acid sequences of wild type AT can be accepted in the present invention. And further, such amino acid sequence that has one or more residues out of 11 residues at amino terminal substituted or deleted can also be accepted. Particularly, the wild type AT produced in *E. coli* exhibited that methionine is located in front of the first amino acid (glutamate) or takes the place of the glutamate or in the case of one or more residues out of 11 resides at amino terminal are deleted, methionine can be added to the N-terminal.

Regardless of the deletion or addition of amino acids, the amino acid of AT of the invention is represented by the amino acid sequence of FIG. 1.

Human alpha-1-antitrypsin can include a mutant AT, in addition to the wild type AT. It is preferred for the mutant AT to include AT mutein to increase heat-resistance or to increase AT activity, but not always limited thereto. It is more preferred for the mutant AT to include the following amino acid variations:

$Ala^{70} \rightarrow Gly^{70}$, $Ala^{142} \rightarrow Val^{142}$, $Gly^{164} \rightarrow Val^{164}$, $Ala^{183} \rightarrow Val^{183}$, $Phe^{189} \rightarrow Val^{189}$, $Ala^{248} \rightarrow Val^{248}$, $Lys^{335} \rightarrow Gly^{335}$.

The mutant AT can also include a recombinant AT mutein in which the $51^{st}$ phenylalanine is substituted with leucine and the $374^{th}$ methionine is substituted with isoleucine, but not always limited thereto.

The recombinant AT of the present invention is characterized by the increased thermostability without reducing elastase inhibiting activity, unlike the wild type AT. As shown in Table 1 of Example 2, mutein serine based protease inhibitors have equal activity to the wild type but have significantly increased thermostability, compared with the wild type recombinant inhibitor produced in *E. coli*. Among the many recombinant AT muteins, the recombinant AT mutein of the invention in which the $168^{th}$ amino acid and the $189^{th}$ amino acid are substituted with cysteines which are then oxidized to form a disulfide bond exhibits improved thermostability 11 times the thermostability of the wild type recombinant AT, 3.3 times the thermostability of human blood plasma AT and 1.55 times the thermostability of the conventional wild type AT mutein (the $51^{st}$ phenylalanine is substituted with leucine and the $374^{th}$ methionine is substituted with isoleucine, named as F51L/M374I described in Korean Patent No. 133252) (see FIG. 4 and Table 1).

The human alpha-1-antitrypsin mutein is preferably composed of the amino acid sequence represented by SEQ. ID. NO: 12 in which the $168^{th}$ and the $189^{th}$ amino acids are substituted with cysteines or the amino acid sequence represented by SEQ. ID. NO: 13 in which the above two amino acids are substituted with cysteines and the $232^{nd}$ amino acid is substituted with serine, but not always limited thereto.

The present invention also provides a polynucleotide encoding the alpha-1-antitrypsin mutein and an expression vector containing the same.

The present invention further provides host cells transformed with the expression vector.

The thermostable AT mutein of the present invention can be produced by the processes of transforming a host cell with a vector containing the gene encoding the thermostable AT mutein prepared by site specific mutagenesis and expressing the thermostable AT therein. Or, the thermostable AT mutein of the invention can also be produced by chemical amino acid synthesis.

The codon encoding the amino acid for the substitution of the DNA encoding the thermostable AT mutein is substituted with another codon encoding another amino acid and the rest of the DNA sequence is the DNA encoding the same amino acid sequence as that of the wild type. The DNA sequence encoding the thermostable AT mutein preferably has the substitution of the $168^{th}$ and the $189^{th}$ codons with the codons encoding cysteine and the $232^{nd}$ codon with the codon encoding serine.

In the meantime, there are multiple codons that encode the same amino acid, resulted from codon degeneracy. So, it is well known to those in the art that despite DNAs equally encode the same amino acid sequence, they might have different nucleotide sequences.

Such DNA encoding the thermostable AT mutein can be chemically synthesized or produced from the wild type AT cDNA by site specific mutagenesis.

The DNA encoding the thermostable AT mutein of the present invention can be expressed by using prokaryotic or eukaryotic expression system well known to those in the art (Sambrook et al., Molecular Cloning, A Laboratory Manual, 2nd ed., Cold Spring Harbor Laboratory, Cold Spring Harbor Laboratory Press, USA, 1989).

The unglycosylated AT can be expressed in *E. coli*, preferably *E. coli* BL21(DE3), *E. coli* JM109(DE3), *E. coli* NM522, etc. Proper vectors for the expression can be selected among those described in papers of Sambrook, et al. and Fiers, et al. ("Proceed. $8^{th}$ Int. Biotechnology Symposium", Soc. Frac, de Microbiol., Paris, (Durand et al., eds.), pp. 680-697, 1988).

Transformation of a host cell with the above vector can be performed by one of the conventional methods (Sambrook, et al., Molecular Cloning, A Laboratory Manual, 1989; Ito et al., J. Bacteriol. 153:263, 1983).

In the case of transforming *E. coli*., competent cells absorbing DNA are prepared according to the conventional method using $CaCl_2$.

In general, a host microorganism containing the target expression vector is cultured in the optimum growth condition to maximize the production of the target protein. For example, *E. coli* BL21(DE3) transformed with the vector containing ampicillin resistance gene as a selection marker is cultured in LB medium containing ampicillin at 37° C.

The recovery and purification of AT produced by the culture of the transformed host cells can be performed by one of the conventional methods known to those in the art. For example, the recombinant AT expressed in the transformed *E. coli* cells can be recovered from the cell culture solution or after cell lysis by a proper method selected by those in the art. Korean Patent Publication No. 93-686 describes the method for purifying the recombinant AT.

Particularly, the recombinant *E. coli* cell culture solution was centrifuged to collect cells, which were resuspended in a buffer containing lysozyme, followed by lysis by sonication. The cell lysate was centrifuged to obtain an insoluble precipitate containing granulated AT. The precipitate was suspended in a buffer containing Triton x-100 and then the precipitate was recovered, which was repeated two times. The precipitate was dissolved in a suspension containing urea, which was diluted with potassium phosphate solution containing ethylenediamine-4-acetate and mercaptoethanol. After dialysis in a phosphate buffer containing ethylenediamine-4-acetate and mercaptoethanol, the solution proceeded to Q-sepharose column (Pharmacia LKB Biotechnology) equilibrated with the same solution. The buffer solution (50 mM Tris-HCl, pH 8.0) containing 1 mM of oxidized glutathione, which was twice the volume of the column, was added thereto to induce oxidation at room temperature for at least 2 hours, resulting in induction of disulfide bond on the column. Then, the column was washed with the buffer solution B having the volume of three times the volume of the column, followed by extraction of a target protein with the buffer solution B containing 0-600 mM of linear gradient sodium chloride. As shown in FIG. 2, the AT mutein with a disulfide bond (row 5) was obtained.

According to the reports of Lomas et al. (Lomas. D. A. et al., Nature 357, 605-607 (1992); Lomas, D. A., et al., Biochemistry 32, 500-508 (1993)), AT is apt to be polymerized or inactivated to be aggregated at high temperature ($\geq 41°$ C.) or even under a weak denaturation condition, which is known as thermal inactivation.

In this invention, aggregation was compared between the AT mutein having two reduced cysteines without a disulfide bond and the AT mutein with a disulfide bond by oxidation. First, each recombinant AT was cultured in a 60° C. oven at the concentration of 0.2 mg/ml. The recombinant AT was taken at each designated time point to be cooled in ice, followed by observation of aggregation by Native-electrophoresis. Aggregation is caused when molecular weight is increased, that is a high molecular weight protein is formed. So, it is located on the upper part of Native gel and has shorter moving distance than the earlier monomer form.

As shown in FIG. 3, the AT mutein of the present invention in which the $168^{th}$ and the $189^{th}$ amino acids are substituted with cysteines and oxidized to form an intramolecular disulfide bond was polymerized at a very low rate, compared with the AT mutein having reduced cysteines without a disulfide bond. This result indicates that the disulfide bond between the $168^{th}$ and the $189^{th}$ cysteine residues inhibits the AT inactivation by polymerization.

Almost all the AT muteins without disulfide bonds were aggregated 30 minutes later, suggesting that they were changed into inactive high molecular proteins. In the meantime, those AT muteins with disulfide bonds still remained as active proteins up to 240 minutes.

ADVANTAGEOUS EFFECT

The AT mutein with a disulfide bond having improved thermostability of the present invention is acting as an inhibitor to elastase of neutrophiles, particularly it prevents elastic fibers in lung sacs from being degraded by elastase, making it as a promising candidate for a preventive and therapeutic agent for emphysema caused by genetic defection or environmental pollution. The strategy of the present invention can be applied to improve the thermostability of other serine based protease inhibitors. The thermostable recombinant inhibitor has increased half-life in blood plasma, compared with the wild type recombinant inhibitor, and thus favors industrialization.

The composition of the thermostable inhibitor can be applied in various fields such as injection, aerosol inhalation, gene therapy, diagnostic reagent, affinity column, etc.

DESCRIPTION OF DRAWINGS

The application of the preferred embodiments of the present invention is best understood with reference to the accompanying drawings, wherein:

FIG. 1 is a diagram showing the amino acid sequence of wild type human alpha-1-antitrypsin.

FIG. 2 is a diagram showing the results of 10% SDS-electrophoresis with the recombinant alpha-1-antitrypsin samples separated and purified from *E. coli* from each representative stage. Lane 1 and lane 10 are standard proteins, lane 2 is total cell lysate, lane 3 is the precipitate containing AT obtained from centrifugation after cell lysis, lane 4 is the recombinant AT mutein purified by Q-sepharose column without oxidation process (the $168^{th}$ and the $189^{th}$ amino acid residues are substituted with cysteines), lane 5 is the recombinant AT mutein purified by Q-sepharose column after oxidation (the $168^{th}$ and the $189^{th}$ amino acid residues are substituted with cysteines), lane 6 is the protein sample of lane 5 which was reduced again after adding mercaptoethanol, lane 7 is the wild type recombinant AT, lane 8 is the conventional recombinant AT (the $51^{st}$ leucine, the $374^{th}$ isoleucine, described in Korean Patent No. 133252), and lane 9 is the human blood plasma AT.

FIG. 4 is a graph showing the comparison of aggregation between the thermostable AT mutein in which the $168^{th}$ and the $189^{th}$ amino acid residues were substituted with cysteines and linked by a disulfide bond and the conventional AT mutein, for which thermal inactivation test was performed at 60° C. during the storage.

MODE FOR INVENTION

Figure 3:
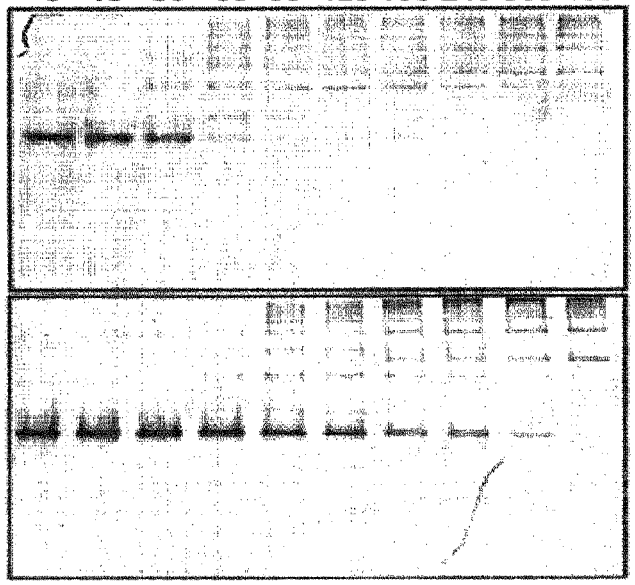
FIG. 3 is a diagram showing the results of Native-electrophoresis with a high molecular protein generated during the storage of the recombinant alpha-1-antitrypsin mutein at 60° C., in which the $168^{th}$ and the $189^{th}$ amino acid residues were substituted with cysteines and reduced or in which the $168^{th}$ and the $189^{th}$ amino acid residues were substituted with cysteines and oxidized to form a disulfide bond.

Practical and presently preferred embodiments of the present invention are illustrative as shown in the following Reference Examples, Manufacturing Examples and Examples.

However, it will be appreciated that those skilled in the art, on consideration of this disclosure, may make modifications and improvements within the spirit and scope of the present invention.

All the DNA manipulation techniques used in this invention are described in the reference of Sambrook, et al. (Molecular Cloning, Cold Spring Harbor Lab (1989)). Restriction enzymes were purchased from New England Biolabs or Boeringer Mannheim.

Methods for measuring the AT activity and thermostability used in the following Reference Examples and Examples of the invention are described hereinafter.

The method for measuring the AT activity used in this invention is to analyze how the AT could inhibit the peptide degradation by elastase. Particularly, elastase dissolved solution and AT extract were mixed with reaction buffer containing glycerol (tris-HCl, pH 8.0), followed by reaction. Substrate buffer (succinyl-alanyl-alanyl-alanyl-para-nitroanilide (Sigma S4760) dissolved in dimethylsulfoxide) was added thereto, followed by measuring $OD_{410}$ to evaluate elastase inhibitory activity of the AT. To measure the thermostability, the purified AT was heat-treated at 60° C. at the concentration of 0.2 mg/ml, followed by measuring elastase inhibitory activity of the AT. The wild type recombinant AT and the AT separated and purified from human blood were used as controls.

Reference Example 1

AT Gene Cloning 32 positive clones were obtained from human liver cDNA library (Clontech, U.S.A) by using the nucleotide number 50-72 probe among nucleotide sequences reported by Long et al. (Long et al., Biochemistry 23, 4828 (1984)), which were narrowed down to 4 positive clones by suing the nucleotide number 1150-1172 probe. pUC-AT(R) was obtain therefrom and AT gene was 1.3 kb fragment cut by EcoRI or BamHI.

More details are described in the reference paper of Lee and Yu (Lee and Yu, Journal of Biochemistry and Molecular Biology 22, 148 (1989)), which is included in this description as a reference.

Reference Example 2

Expression of Wild Type Recombinant AT

The pUC-AT(R) prepared in Reference Example 1 was digested with BamHI to obtain 1.3 kb fragment, which was inserted into BamHI site of pET-8c plasmid (Studier and Moffatt. J. Mol. Biol, 189, 112 (1986)) to construct pEAT 8. *E. coli* BL21(DE3) was transformed with the pEAT 8 and the expressed AT was named as wild type *E. coli* recombinant AT. The wild type *E. coli* recombinant AT polypeptide contains methionine as the first residue of amino acid sequence, while human blood plasma originated AT contains glutamate as the first amino acid residue. However, the remaining residues from the second residue were same as those of wild type AT (FIG. 1).

The amino terminal sequence of the wild type recombinant AT was confirmed by protein sequencing (Applied Biosystem 477A was used). The *E. coli* transformed with pEAT 8 was deposited at Korean Collection for Type Cultures on Apr. 17, 1991 (Accession No: KCTC 0009BP).

The details on this example are described in Korean Patent Publication No. 93-686. This description is also included in this invention as a reference.

Manufacturing Example 1

Construction of a Transformant Containing a Gene Substituted to Produce Thermostable AT Site specific mutagenesis was induced according to the modified PCR developed by EcKert et al. (Eckert and Kunkel, PCR Chap. 14, The fidelity of DNA polymerase chain reactions, ed. by McPharson et al., Oxford Univ. Press (1991)). Particularly, a primer (approximately 30 mer) was designed to have single stranded DNA obtained from pEAT 8 plasmid prepared in Reference Example 2 and the substituted codon corresponding to the amino acid in the center, and used for the site specific mutagenesis according to the method of Kunkel (Kunkel, Methods in enzymol. 154. 367-382 (1987)). The mutation was confirmed by nucleotide sequencing.

*E. coli* BL21(DE3) was transformed with the constructed plasmid and then mutant strain was obtained from the colony having ampicillin resistance.

Example 1

Preparation of a Site Specific Mutant Gene

An attempt to change the structure of AT was made to inhibit the activity of protease by introducing a disulfide bond artificially in the AT molecule. Mutein was prepared by substituting the properly selected amino acid pair with cysteines and oxidation was induced therein to form a disulfide bond. To investigate the effect of structural changes by limiting the movement of protein structure, several pairs of amino acids substituted with two cysteines were prepared. The $232^{nd}$ cysteine was substituted with serine to avoid any side reactions during oxidation. To obtain the substituent for the corresponding amino acids, oligonucleotide mediated site specific mutagenesis was used (Kunkel et al., Methods in Enzymology 154, 367-382 (1987)).

The oligonucleotide for inducing mutation is composed of 27-30 nucleotides and is designed to have the code of cysteine or serine in the place of the $168^{th}$, $189^{th}$ or $232^{nd}$ residue and to have the code of wild type amino acid residues for the rest. 1) Oligonucleotide having cysteine in the place of the $168^{th}$ lysine (AAA): $^{165}$ACT CAA GGG TGT ATT GTG GAT TTG GTC$^{173}$ (SEQ. ID. NO: 9), 2) Oligonucleotide having cysteine in the place of the $189^{th}$ phenylalanine (TTC): $^{186}$AAT TAC ATC TGC TTT AAA TGG GAG AGA CCC$^{197}$ (SEQ. ID. NO: 10), 3) Oligonucleotide having serine in the place of the $232^{nd}$ cysteine (TGT): $^{229}$ATC CAG CAC TCT AAG AAG CTG TCC AGC$^{237}$ (SEQ. ID. NO: 11). M13 clone of AT gene was amplifying cultured three times in LB medium supplemented with 0.25 µg/ml of uridine using $E.\ coli$ CJ236 (dut-, ung-, Boeringer Mannheim) as a host to obtain bacteriophage particles. Single stranded uridine template was obtained from the bacteriophage particles. Synthetic oligonucleotide was linked thereto, which was used for the transformation of $E.\ coli$ JM109 (ATCC 53323). Wild type template was selectively eliminated to obtain the mutant clone. Replicative form (RF) DNA was obtained from the clone, with which mutein expression vector was constructed. $E.\ coli$ BL21(DE3) was transformed with the vector. Nucleotide sequencing was performed with the vector and as a result it was confirmed that the $168^{th}$ and the $189^{th}$ amino acids were substituted with cysteines and the $232^{nd}$ amino acid was substituted with serine.

Example 2

Separation and Purification of the Recombinant AT and Characteristics thereof

<2-1> Separation and Purification of the Recombinant AT

Separation and purification was performed according to modified method based on Korean Patent Publication No. 93-686. The AT mutein strain in which the $168^{th}$ and the $189^{th}$ amino acids were substituted with cysteines prepared in Example 1 was inoculated into 250 ml of M9ZB medium (1 g of ammonium chloride, 3 g of potassium phosphate, 6 g of sodium phosphate, 2 g of glucose, 0.2 g of yeast extract and 3 g of casamino acid were dissolved in 1 l of water), followed by culture at 37° C. until OD$_{600}$ reached 0.8. 0.4 mM of IPTG was added thereto, followed by culture at 40° C. for hours. The culture medium was centrifuged to recover cells, and the collected cells were suspended in buffer A (50 mM tris containing 50 mM sodium chloride, 1 mM ethylenediamine-4-acetate and 1 mM mercaptoethanol, pH 8.0) supplemented with 0.1 mg/ml of lysozyme, followed by lysis by sonication at 0° C. The lysate was centrifuged for 10 minutes (10,000×g) to obtain a precipitate containing insoluble granulated AT. The precipitate was suspended in buffer A containing 0.5% triton X-100 and this suspension was centrifuged to collect the precipitate, which was repeated more than once. The precipitated was dissolved in 5 ml of buffer A containing 8 M urea, which stood for 30 minutes. The mixture was added into 4 l of buffer B (1 mM ethylenediamine-4-acetate and 1 mM mercaptoethanol, 50 mM phosphate, pH 6.5) slowly for dilution. Then, the mixture proceeded to Q sepharose column (Amersharm-Pharmacia) equilibrated with buffer B. The 50 mM Tris-HCl buffer containing 1 mM of oxidized glutathione, which was twice the volume of the column, was added thereto to induce oxidation at room temperature for at least 2 hours, resulting in induction of disulfide bond on the column. Then, the column was washed with the buffer solution B having the volume of three times the volume of the column. The target protein was eluted with the buffer solution B containing 0-600 mM of linear gradient sodium chloride followed by 10% SDS-electrophoresis. As a result, the recombinant AT with a pure disulfide bond was obtained (lane 5, FIG. 2).

As shown in FIG. 2, the movement of the recombinant AT with a disulfide bond on SDS-electrophoresis was faster (absence of a reducing agent) than the recombinant AT mutein without oxidation or the recombinant AT mutein reduced again after induction of disulfide bond.

<2-2> Thermostability of the AT Mutein

Heat-resistance was investigated with the recombinant AT prepared by substituting the $168^{th}$ and the $189^{th}$ amino acid residues with cysteines and having a disulfide bond therein. To compare the activity and thermostability of the recombinant AT with that of purified human blood plasma AT, coupling constant to elastase and thermal inactivation rate were examined. The human blood plasma AT (A9204, Sigma) purified with Affi-Gel Blue column (Bio-Rad) and HPLC mono Q column.

Coupling constant was measured according to the method of Beatty et al (Beatty et al., J. Biol. Chem. 255, 3931-3934 (1980)). Particularly, reaction mixture containing equal concentration (8 nM) of elastase and the AT was taken at every designated time point (1-10 minutes), and 1 mm of succinyl-alanyl-alanyl-alanyl-paranitroanilide (Sigma A4760) was added as a substrate and the elastase activity was measured at 410 nm. Coupling constant was calculated from the slope of a line of a graph obtained from the inverse number of the elastase concentration over the time.

As shown in Table 1, the wild type and the recombinant AT muteins were confirmed to have similar coupling constants with that of the human blood plasma AT. That is, the AT mutein obtained in the above example had normal activity.

To compare thermostability, each AT was stirred at 60° C. and samples were taken at each designated time point and the remaining AT activity was measured. Half-life and thermal inactivation rate were calculated from the line (FIG. 4) of a graph obtained from the logarithmic values of the remaining activity over the time. And the results are shown in Table 1.

TABLE 1

Coupling constant, half life at 60° C. and thermal inactivation rate of recombinant ATs

| Kinds of ATs | mutant | Coupling constant ($M^{-1} sec^{-1}$) | Half-life (min) | Thermal inactivation rate($sec^{-1}$) |
| --- | --- | --- | --- | --- |
| wild type recombinant AT | — | $1.6 \times 10^6$ | 5.0 | 0.137 |
| Mutant recombinant AT | F51L/ M3741 | $1.7 \times 10^6$ | 35.5 | 0.019 |
| Mutant recombinant AT (with disulfide bond) | K168C/ F189C | $1.8 \times 10^6$ | 55.2 | 0.014 |
| Human blood plasma AT | — | $1.7 \times 10^6$ | 16.8 | 0.049 |

As shown in Table 1, the mutein serine protease inhibitors had equal activity with the wild type and had significantly improved thermostability, compared with the wild type recombinant inhibitor produced in $E.\ coli$. In particular, the recombinant AT prepared by substituting the $168^{th}$ and the 189$^{th}$ amino acids with cysteines and inducing disulfide bond therein exhibited improved thermostability 11 times the thermostability of the wild type recombinant AT, 3.3 times the thermostability of the human blood plasma AT and 1.6 times the thermostability of the conventional recombinant AT (Recombinant AT mutein in which the 51$^{st}$ phenylalanine is substituted with leucine, and the 374$^{th}$ methionine is substituted with isoleucine).

<2-3> Inhibition of Aggregation by the AT Mutein with a Disulfide Bond

According to the reports of Lomas et al. (Lomas. D. A. et al., Nature 357, 605-607 (1992); Lomas, D. A., et al., Biochemistry 32, 500-508 (1993)), AT is apt to be polymerized or inactivated to be aggregated at high temperature (≧41° C.) or even under a weak denaturation condition, which is known as thermal inactivation.

In this invention, aggregation was compared between the AT mutein having two reduced cysteines without a disulfide bond and the AT mutein with a disulfide bond by oxidation. First, each recombinant AT was cultured in a 60° C. oven at the concentration of 0.2 mg/ml. The culture was taken at each designated time point to be cooled in ice, followed by observation of aggregation by Native-electrophoresis. Aggregation is caused when molecular weight is increased, that is a high molecular weight protein is formed. So, it is located on the upper part of Native gel and has shorter moving distance than the earlier monomer form.

As shown in FIG. 3, the AT mutein of the present invention in which the 168$^{th}$ and the 189$^{th}$ amino acids are substituted with cysteines and oxidized to form an intramolecular disulfide bond was polymerized at a very low rate, compared with the AT mutein having reduced cysteines without a disulfide bond. This result indicates that the disulfide bond between the 168$^{th}$ and the 189$^{th}$ cysteine residues inhibits the AT inactivation by polymerization.

Almost all the AT muteins without disulfide bonds were aggregated 30 minutes later, suggesting that they were changed into inactive high molecular proteins. In the meantime, those AT muteins with disulfide bonds still remained as active proteins up to 240 minutes.

Those skilled in the art will appreciate that the conceptions and specific embodiments disclosed in the foregoing description may be readily utilized as a basis for modifying or designing other embodiments for carrying out the same purposes of the present invention. Those skilled in the art will also appreciate that such equivalent embodiments do not depart from the spirit and scope of the invention as set forth in the appended claims.

The invention claimed is:

1. A polynucleotide encoding a human alpha-1-antitrypsin mutein comprising an amino acid sequence selected from the group consisting of the amino acid sequence of SEQ ID NO:12 and the amino acid sequence of SEQ ID NO:13.

2. The polynucleotide according to claim 1, wherein the polynucleotide encodes a human alpha-1-antitrypsin mutein comprising the amino acid sequence of SEQ ID NO:12.

3. An expression vector comprising the polynucleotide of claim 1.

4. An isolated host cell transformed with the expression vector of claim 3.

5. A method of preparing a thermostable human alpha-1-antitrypsin (AT) mutein comprising the following steps:
  1) culturing the isolated host cell of claim 4 in a culture solution to produce an AT mutein comprising an amino acid sequence selected from the group consisting of the amino acid sequence of SEQ ID NO:12 and the amino acid sequence of SEQ ID NO:13;
  2) adding the AT mutein produced in the culture solution to a purification column;
  3) oxidizing the AT mutein on the column to form a thermostable AT mutein with a disulfide bond; and
  4) eluting the thermostable AT mutein with a disulfide bond from the column.

6. The method of claim 5, wherein in step 4) the thermostable AT mutein with a disulfide bond is eluted from the column by using a sodium chloride density gradient.

7. The method of claim 5, wherein the produced AT mutein comprises the amino acid sequence of SEQ ID NO:12.

8. The method of claim 5, wherein the produced AT mutein comprises the amino acid sequence of SEQ ID NO:13.

9. The polynucleotide according to claim 1, wherein the polynucleotide encodes a human alpha-1-antitrypsin mutein comprising the amino acid sequence of SEQ ID NO:13.

10. The expression vector according to claim 3, wherein the expression vector is bacteriophage M13 comprising the polynucleotide.

11. The expression vector according to claim 3, wherein the polynucleotide encodes a human alpha-1-antitrypsin mutein comprising the amino acid sequence of SEQ ID NO:12.

12. The expression vector according to claim 3, wherein the polynucleotide encodes a human alpha-1-antitrypsin mutein comprising the amino acid sequence of SEQ ID NO:13.

13. The isolated host cell according to claim 4, wherein the polynucleotide of the expression vector encodes a human alpha-1-antitrypsin mutein comprising the amino acid sequence of SEQ ID NO:12.

14. The isolated host cell according to claim 4, wherein the polynucleotide of the expression vector encodes a human alpha-1-antitrypsin mutein comprising the amino acid sequence of SEQ ID NO:13.

15. The isolated host cell according to claim 4, wherein the isolated host cell is an *Escherichia coli* host cell.

* * * * *

SEQUENCE LISTING

```
<160> NUMBER OF SEQ ID NOS: 13

<210> SEQ ID NO 1
<211> LENGTH: 394
<212> TYPE: PRT
<213> ORGANISM: Homo sapiens

<400> SEQUENCE: 1

Glu Asp Pro Gln Gly Asp Ala Ala Gln Lys Thr Asp Thr Ser His His
1               5                   10                  15

Asp Gln Asp His Pro Thr Phe Asn Lys Ile Thr Pro Asn Leu Ala Glu
            20                  25                  30

Phe Ala Phe Ser Leu Tyr Arg Gln Leu Ala His Gln Ser Asn Ser Thr
        35                  40                  45

Asn Ile Phe Phe Ser Pro Val Ser Ile Ala Thr Ala Phe Ala Met Leu
    50                  55                  60

Ser Leu Gly Thr Lys Ala Asp Thr His Asp Glu Ile Leu Glu Gly Leu
65                  70                  75                  80

Asn Phe Asn Leu Thr Glu Ile Pro Glu Ala Gln Ile His Glu Gly Phe
                85                  90                  95

Gln Glu Leu Leu Arg Thr Leu Asn Gln Pro Asp Ser Gln Leu Gln Leu
            100                 105                 110

Thr Thr Gly Asn Gly Leu Phe Leu Ser Glu Gly Leu Lys Leu Val Asp
        115                 120                 125

Lys Phe Leu Glu Asp Val Lys Lys Leu Tyr His Ser Glu Ala Phe Thr
    130                 135                 140

Val Asn Phe Gly Asp Thr Glu Glu Ala Lys Lys Gln Ile Asn Asp Tyr
145                 150                 155                 160

Val Glu Lys Gly Thr Gln Gly Lys Ile Val Asp Leu Val Lys Glu Leu
                165                 170                 175

Asp Arg Asp Thr Val Phe Ala Leu Val Asn Tyr Ile Phe Phe Lys Gly
            180                 185                 190

Lys Trp Glu Arg Pro Phe Glu Val Lys Asp Thr Glu Glu Glu Asp Phe
```

-continued

```
                195                 200                 205
His Val Asp Gln Val Thr Thr Val Lys Val Pro Met Met Lys Arg Leu
    210                 215                 220

Gly Met Phe Asn Ile Gln His Cys Lys Lys Leu Ser Ser Trp Val Leu
225                 230                 235                 240

Leu Met Lys Tyr Leu Gly Asn Ala Thr Ala Ile Phe Phe Leu Pro Asp
                245                 250                 255

Glu Gly Lys Leu Gln His Leu Glu Asn Glu Leu Thr His Asp Ile Ile
                260                 265                 270

Thr Lys Phe Leu Glu Asn Glu Asp Arg Arg Ser Ala Ser Leu His Leu
    275                 280                 285

Pro Lys Leu Ser Ile Thr Gly Thr Tyr Asp Leu Lys Ser Val Leu Gly
    290                 295                 300

Gln Leu Gly Ile Thr Lys Val Phe Ser Asn Gly Ala Asp Leu Ser Gly
305                 310                 315                 320

Val Thr Glu Glu Ala Pro Leu Lys Leu Ser Lys Ala Val His Lys Ala
                325                 330                 335

Val Leu Thr Ile Asp Glu Lys Gly Thr Glu Ala Ala Gly Ala Met Phe
                340                 345                 350

Leu Glu Ala Ile Pro Met Ser Ile Pro Pro Glu Val Lys Phe Asn Lys
            355                 360                 365

Pro Phe Val Phe Leu Met Ile Glu Gln Asn Thr Lys Ser Pro Leu Phe
    370                 375                 380

Met Gly Lys Val Val Asn Pro Thr Gln Lys
385                 390

<210> SEQ ID NO 2
<211> LENGTH: 394
<212> TYPE: PRT
<213> ORGANISM: Homo sapiens

<400> SEQUENCE: 2

Glu Asp Pro Gln Gly Asp Ala Ala Gln Lys Thr Asp Thr Ser His His
1               5                   10                  15

Asp Gln Asp His Pro Thr Phe Asn Lys Ile Thr Pro Asn Leu Ala Glu
                20                  25                  30

Phe Ala Phe Ser Leu Tyr Arg Gln Leu Ala His Gln Ser Asn Ser Thr
            35                  40                  45

Asn Ile Phe Phe Ser Pro Val Ser Ile Ala Thr Ala Phe Ala Met Leu
        50                  55                  60

Ser Leu Gly Thr Lys Ala Asp Thr His Asp Glu Ile Leu Glu Gly Leu
65              70                  75                  80

Asn Phe Asn Leu Thr Glu Ile Pro Glu Ala Gln Ile His Glu Gly Phe
                85                  90                  95

Gln Glu Leu Leu His Thr Leu Asn Gln Pro Asp Ser Gln Leu Gln Leu
            100                 105                 110

Thr Thr Gly Asn Gly Leu Phe Leu Ser Glu Gly Leu Lys Leu Val Asp
        115                 120                 125

Lys Phe Leu Glu Asp Val Lys Lys Leu Tyr His Ser Glu Ala Phe Thr
    130                 135                 140

Val Asn Phe Gly Asp Thr Glu Glu Ala Lys Lys Gln Ile Asn Asp Tyr
145                 150                 155                 160

Val Glu Lys Gly Thr Gln Gly Lys Ile Val Asp Leu Val Lys Glu Leu
                165                 170                 175

Asp Arg Asp Thr Val Phe Ala Leu Val Asn Tyr Ile Phe Phe Lys Gly
```

```
                    180                 185                 190
Lys Trp Glu Arg Pro Phe Glu Val Lys Asp Thr Glu Glu Asp Phe
            195                 200                 205

His Val Asp Gln Val Thr Thr Val Lys Val Pro Met Met Lys Arg Leu
210                 215                 220

Gly Met Phe Asn Ile Gln His Cys Lys Lys Leu Ser Ser Trp Val Leu
225                 230                 235                 240

Leu Met Lys Tyr Leu Gly Asn Ala Thr Ala Ile Phe Phe Leu Pro Asp
            245                 250                 255

Glu Gly Lys Leu Gln His Leu Glu Asn Glu Leu Thr His Asp Ile Ile
            260                 265                 270

Thr Lys Phe Leu Glu Asn Glu Asp Arg Arg Ser Ala Ser Leu His Leu
            275                 280                 285

Pro Lys Leu Ser Ile Thr Gly Thr Tyr Asp Leu Lys Ser Val Leu Gly
            290                 295                 300

Gln Leu Gly Ile Thr Lys Val Phe Ser Asn Gly Ala Asp Leu Ser Gly
305                 310                 315                 320

Val Thr Glu Glu Ala Pro Leu Lys Leu Ser Lys Ala Val His Lys Ala
                325                 330                 335

Val Leu Thr Ile Asp Glu Lys Gly Thr Glu Ala Ala Gly Ala Met Phe
            340                 345                 350

Leu Glu Ala Ile Pro Met Ser Ile Pro Pro Glu Val Lys Phe Asn Lys
            355                 360                 365

Pro Phe Val Phe Leu Met Ile Glu Gln Asn Thr Lys Ser Pro Leu Phe
            370                 375                 380

Met Gly Lys Val Val Asn Pro Thr Gln Lys
385                 390

<210> SEQ ID NO 3
<211> LENGTH: 394
<212> TYPE: PRT
<213> ORGANISM: Homo sapiens

<400> SEQUENCE: 3

Glu Asp Pro Gln Gly Asp Ala Ala Gln Lys Thr Asp Thr Ser His His
1               5                   10                  15

Asp Gln Asp His Pro Thr Phe Asn Lys Ile Thr Pro Asn Leu Ala Glu
            20                  25                  30

Phe Ala Phe Ser Leu Tyr Arg Gln Leu Ala His Gln Ser Asn Ser Thr
        35                  40                  45

Asn Ile Phe Phe Ser Pro Val Ser Ile Ala Thr Ala Phe Ala Met Leu
50                  55                  60

Ser Leu Gly Thr Lys Ala Asp Thr His Asp Glu Ile Leu Glu Gly Leu
65                  70                  75                  80

Asn Phe Asn Leu Thr Glu Ile Pro Glu Ala Gln Ile His Glu Gly Phe
            85                  90                  95

Gln Glu Leu Leu Arg Thr Leu Asn Gln Pro Asp Ser Gln Leu Gln Leu
        100                 105                 110

Thr Thr Gly Asn Gly Leu Phe Leu Ser Glu Gly Leu Lys Leu Val Asp
    115                 120                 125

Lys Phe Leu Glu Asp Val Lys Lys Leu Tyr His Ser Glu Ala Phe Thr
130                 135                 140

Val Asn Phe Gly Asp Thr Glu Glu Ala Lys Lys Gln Ile Asn Asp Tyr
145                 150                 155                 160

Val Glu Lys Gly Thr Gln Gly Lys Ile Val Asp Leu Val Lys Glu Leu
```

```
                      165                 170                 175
Asp Arg Asp Thr Val Phe Ala Leu Val Asn Tyr Ile Phe Phe Lys Gly
                180                 185                 190

Lys Trp Glu Arg Pro Phe Glu Val Lys Asp Thr Lys Glu Glu Asp Phe
            195                 200                 205

His Val Asp Gln Val Thr Thr Val Lys Val Pro Met Met Lys Arg Leu
        210                 215                 220

Gly Met Phe Asn Ile Gln His Cys Lys Lys Leu Ser Ser Trp Val Leu
225                 230                 235                 240

Leu Met Lys Tyr Leu Gly Asn Ala Thr Ala Ile Phe Phe Leu Pro Asp
                245                 250                 255

Glu Gly Lys Leu Gln His Leu Glu Asn Glu Leu Thr His Asp Ile Ile
            260                 265                 270

Thr Lys Phe Leu Glu Asn Glu Asp Arg Arg Ser Ala Ser Leu His Leu
        275                 280                 285

Pro Lys Leu Ser Ile Thr Gly Thr Tyr Asp Leu Lys Ser Val Leu Gly
        290                 295                 300

Gln Leu Gly Ile Thr Lys Val Phe Ser Asn Gly Ala Asp Leu Ser Gly
305                 310                 315                 320

Val Thr Glu Glu Ala Pro Leu Lys Leu Ser Lys Ala Val His Lys Ala
                325                 330                 335

Val Leu Thr Ile Asp Glu Lys Gly Thr Glu Ala Ala Gly Ala Met Phe
            340                 345                 350

Leu Glu Ala Ile Pro Met Ser Ile Pro Pro Glu Val Lys Phe Asn Lys
        355                 360                 365

Pro Phe Val Phe Leu Met Ile Glu Gln Asn Thr Lys Ser Pro Leu Phe
    370                 375                 380

Met Gly Lys Val Val Asn Pro Thr Gln Lys
385                 390

<210> SEQ ID NO 4
<211> LENGTH: 394
<212> TYPE: PRT
<213> ORGANISM: Homo sapiens

<400> SEQUENCE: 4

Glu Asp Pro Gln Gly Asp Ala Ala Gln Lys Thr Asp Thr Ser His His
1               5                   10                  15

Asp Gln Asp His Pro Thr Phe Asn Lys Ile Thr Pro Asn Leu Ala Glu
            20                  25                  30

Phe Ala Phe Ser Leu Tyr Arg Gln Leu Ala His Gln Ser Asn Ser Thr
        35                  40                  45

Asn Ile Phe Phe Ser Pro Val Ser Ile Ala Thr Ala Phe Ala Met Leu
    50                  55                  60

Ser Leu Gly Thr Lys Ala Asp Thr His Asp Glu Ile Leu Glu Gly Leu
65                  70                  75                  80

Asn Phe Asn Leu Thr Glu Ile Pro Glu Ala Gln Ile His Glu Gly Phe
                85                  90                  95

Gln Glu Leu Leu Arg Thr Leu Asn Gln Pro Asp Ser Gln Leu Gln Leu
            100                 105                 110

Thr Thr Gly Asn Gly Leu Phe Leu Ser Glu Gly Leu Lys Leu Val Asp
        115                 120                 125

Lys Phe Leu Glu Asp Val Lys Lys Leu Tyr His Ser Glu Ala Phe Thr
    130                 135                 140

Val Asn Phe Gly Asp Thr Glu Glu Ala Lys Lys Gln Ile Asn Asp Tyr
```

```
                145                 150                 155                 160
Val Glu Lys Gly Thr Gln Gly Lys Ile Val Asp Leu Val Lys Glu Leu
                    165                 170                 175

Asp Arg Asp Thr Val Phe Ala Leu Val Asn Tyr Ile Phe Phe Lys Gly
                180                 185                 190

Lys Trp Glu Arg Pro Phe Glu Val Lys Asp Thr Glu Glu Asp Phe
            195                 200                 205

His Val Asp Gln Ala Thr Thr Val Lys Val Pro Met Met Lys Arg Leu
        210                 215                 220

Gly Met Phe Asn Ile Gln His Cys Lys Lys Leu Ser Ser Trp Val Leu
225                 230                 235                 240

Leu Met Lys Tyr Leu Gly Asn Ala Thr Ala Ile Phe Phe Leu Pro Asp
                245                 250                 255

Glu Gly Lys Leu Gln His Leu Glu Asn Glu Leu Thr His Asp Ile Ile
                260                 265                 270

Thr Lys Phe Leu Glu Asn Glu Asp Arg Arg Ser Ala Ser Leu His Leu
            275                 280                 285

Pro Lys Leu Ser Ile Thr Gly Thr Tyr Asp Leu Lys Ser Val Leu Gly
        290                 295                 300

Gln Leu Gly Ile Thr Lys Val Phe Ser Asn Gly Ala Asp Leu Ser Gly
305                 310                 315                 320

Val Thr Glu Glu Ala Pro Leu Lys Leu Ser Lys Ala Val His Lys Ala
                325                 330                 335

Val Leu Thr Ile Asp Glu Lys Gly Thr Glu Ala Ala Gly Ala Met Phe
                340                 345                 350

Leu Glu Ala Ile Pro Met Ser Ile Pro Pro Glu Val Lys Phe Asn Lys
            355                 360                 365

Pro Phe Val Phe Leu Met Ile Glu Gln Asn Thr Lys Ser Pro Leu Phe
        370                 375                 380

Met Gly Lys Val Val Asn Pro Thr Gln Lys
385                 390

<210> SEQ ID NO 5
<211> LENGTH: 394
<212> TYPE: PRT
<213> ORGANISM: Homo sapiens

<400> SEQUENCE: 5

Glu Asp Pro Gln Gly Asp Ala Ala Gln Lys Thr Asp Thr Ser His His
1               5                   10                  15

Asp Gln Asp His Pro Thr Phe Asn Lys Ile Thr Pro Asn Leu Ala Glu
            20                  25                  30

Phe Ala Phe Ser Leu Tyr Arg Gln Leu Ala His Gln Ser Asn Ser Thr
        35                  40                  45

Asn Ile Phe Phe Ser Pro Val Ser Ile Ala Thr Ala Phe Ala Met Leu
    50                  55                  60

Ser Leu Gly Thr Lys Ala Asp Thr His Asp Glu Ile Leu Glu Gly Leu
65                  70                  75                  80

Asn Phe Asn Leu Thr Glu Ile Pro Glu Ala Gln Ile His Glu Gly Phe
                85                  90                  95

Gln Glu Leu Leu Arg Thr Leu Asn Gln Pro Asp Ser Gln Leu Gln Leu
            100                 105                 110

Thr Thr Gly Asn Gly Leu Phe Leu Ser Glu Gly Leu Lys Leu Val Asp
        115                 120                 125

Lys Phe Leu Glu Asp Val Lys Lys Leu Tyr His Ser Glu Ala Phe Thr
```

```
                    130                 135                 140
Val Asn Phe Gly Asp Thr Glu Ala Lys Lys Gln Ile Asn Asp Tyr
145                 150                 155                 160

Val Glu Lys Gly Thr Gln Gly Lys Ile Val Asp Leu Val Lys Glu Leu
                165                 170                 175

Asp Arg Asp Thr Val Phe Ala Leu Val Asn Tyr Ile Phe Phe Lys Gly
                180                 185                 190

Lys Trp Glu Arg Pro Phe Glu Val Lys Asp Thr Glu Glu Asp Phe
                195                 200                 205

His Val Asp Gln Val Thr Thr Val Lys Val Pro Met Met Lys Cys Leu
210                 215                 220

Gly Met Phe Asn Ile Gln His Cys Lys Lys Leu Ser Ser Trp Val Leu
225                 230                 235                 240

Leu Met Lys Tyr Leu Gly Asn Ala Thr Ala Ile Phe Phe Leu Pro Asp
                245                 250                 255

Glu Gly Lys Leu Gln His Leu Glu Asn Glu Leu Thr His Asp Ile Ile
                260                 265                 270

Thr Lys Phe Leu Glu Asn Glu Asp Arg Arg Ser Ala Ser Leu His Leu
                275                 280                 285

Pro Lys Leu Ser Ile Thr Gly Thr Tyr Asp Leu Lys Ser Val Leu Gly
                290                 295                 300

Gln Leu Gly Ile Thr Lys Val Phe Ser Asn Gly Ala Asp Leu Ser Gly
305                 310                 315                 320

Val Thr Glu Glu Ala Pro Leu Lys Leu Ser Lys Ala Val His Lys Ala
                325                 330                 335

Val Leu Thr Ile Asp Glu Lys Gly Thr Glu Ala Ala Gly Ala Met Phe
                340                 345                 350

Leu Glu Ala Ile Pro Met Ser Ile Pro Pro Glu Val Lys Phe Asn Lys
                355                 360                 365

Pro Phe Val Phe Leu Met Ile Glu Gln Asn Thr Lys Ser Pro Leu Phe
                370                 375                 380

Met Gly Lys Val Val Asn Pro Thr Gln Lys
385                 390

<210> SEQ ID NO 6
<211> LENGTH: 394
<212> TYPE: PRT
<213> ORGANISM: Homo sapiens

<400> SEQUENCE: 6

Glu Asp Pro Gln Gly Asp Ala Ala Gln Lys Thr Asp Thr Ser His His
1               5                   10                  15

Asp Gln Asp His Pro Thr Phe Asn Lys Ile Thr Pro Asn Leu Ala Glu
                20                  25                  30

Phe Ala Phe Ser Leu Tyr Arg Gln Leu Ala His Gln Ser Asn Ser Thr
            35                  40                  45

Asn Ile Phe Phe Ser Pro Val Ser Ile Ala Thr Ala Phe Ala Met Leu
50                  55                  60

Ser Leu Gly Thr Lys Ala Asp Thr His Asp Glu Ile Leu Glu Gly Leu
65                  70                  75                  80

Asn Phe Asn Leu Thr Glu Ile Pro Glu Ala Gln Ile His Glu Gly Phe
                85                  90                  95

Gln Glu Leu Leu Arg Thr Leu Asn Gln Pro Asp Ser Gln Leu Gln Leu
            100                 105                 110

Thr Thr Gly Asn Gly Leu Phe Leu Ser Glu Gly Leu Lys Leu Val Asp
```

```
            115                 120                 125
Lys Phe Leu Glu Asp Val Lys Lys Leu Tyr His Ser Glu Ala Phe Thr
    130                 135                 140

Val Asn Phe Gly Asp Thr Glu Glu Ala Lys Lys Gln Ile Asn Asp Tyr
145                 150                 155                 160

Val Glu Lys Gly Thr Gln Gly Lys Ile Val Asp Leu Val Lys Glu Leu
                165                 170                 175

Asp Arg Asp Thr Val Phe Ala Leu Val Asn Tyr Ile Phe Phe Lys Gly
                180                 185                 190

Lys Trp Glu Arg Pro Phe Glu Val Lys Asp Thr Glu Glu Glu Asp Phe
            195                 200                 205

His Val Asp Gln Val Thr Thr Val Lys Val Pro Met Met Lys Arg Leu
    210                 215                 220

Gly Met Phe Asn Ile Gln His Cys Lys Lys Leu Ser Ser Trp Val Leu
225                 230                 235                 240

Leu Met Lys Tyr Leu Gly Asn Ala Thr Ala Ile Phe Phe Leu Pro Asp
                245                 250                 255

Glu Gly Lys Leu Gln His Leu Glu Asn Glu Leu Thr His Asp Ile Ile
                260                 265                 270

Thr Lys Phe Leu Glu Asn Glu Asp Arg Arg Ser Ala Ser Leu His Leu
            275                 280                 285

Pro Lys Leu Ser Ile Thr Gly Thr Tyr Asp Leu Lys Ser Val Leu Gly
    290                 295                 300

Gln Leu Gly Ile Thr Lys Val Phe Ser Asn Gly Ala Asp Leu Ser Gly
305                 310                 315                 320

Val Thr Glu Glu Ala Pro Leu Lys Leu Ser Lys Ala Val His Lys Ala
                325                 330                 335

Val Leu Thr Ile Asn Glu Lys Gly Thr Glu Ala Ala Gly Ala Met Phe
                340                 345                 350

Leu Glu Ala Ile Pro Met Ser Ile Pro Pro Glu Val Lys Phe Asn Lys
            355                 360                 365

Pro Phe Val Phe Leu Met Ile Glu Gln Asn Thr Lys Ser Pro Leu Phe
    370                 375                 380

Met Gly Lys Val Val Asn Pro Thr Gln Lys
385                 390

<210> SEQ ID NO 7
<211> LENGTH: 394
<212> TYPE: PRT
<213> ORGANISM: Homo sapiens

<400> SEQUENCE: 7

Glu Asp Pro Gln Gly Asp Ala Ala Gln Lys Thr Asp Thr Ser His His
1               5                   10                  15

Asp Gln Asp His Pro Thr Phe Asn Lys Ile Thr Pro Asn Leu Ala Glu
            20                  25                  30

Phe Ala Phe Ser Leu Tyr Arg Gln Leu Ala His Gln Ser Asn Ser Thr
        35                  40                  45

Asn Ile Phe Phe Ser Pro Val Ser Ile Ala Thr Ala Phe Ala Met Leu
    50                  55                  60

Ser Leu Gly Thr Lys Ala Asp Thr His Asp Glu Ile Leu Glu Gly Leu
65                  70                  75                  80

Asn Phe Asn Leu Thr Glu Ile Pro Glu Ala Gln Ile His Glu Gly Phe
                85                  90                  95

Gln Glu Leu Leu Arg Thr Leu Asn Gln Pro Asp Ser Gln Leu Gln Leu
```

```
            100                 105                 110
Thr Thr Gly Asn Gly Leu Phe Leu Ser Glu Gly Leu Lys Leu Val Asp
        115                 120                 125

Lys Phe Leu Glu Asp Val Lys Lys Leu Tyr His Ser Glu Ala Phe Thr
130                 135                 140

Val Asn Phe Gly Asp Thr Glu Glu Ala Lys Lys Gln Ile Asn Asp Tyr
145                 150                 155                 160

Val Glu Lys Gly Thr Gln Gly Lys Ile Val Asp Leu Val Lys Glu Leu
                165                 170                 175

Asp Arg Asp Thr Val Phe Ala Leu Val Asn Tyr Ile Phe Phe Lys Gly
            180                 185                 190

Lys Trp Glu Arg Pro Phe Glu Val Lys Asp Thr Glu Glu Glu Asp Phe
        195                 200                 205

His Val Asp Gln Val Thr Thr Val Lys Val Pro Met Met Lys Arg Leu
    210                 215                 220

Gly Met Phe Asn Ile Gln His Cys Lys Lys Leu Ser Ser Trp Val Leu
225                 230                 235                 240

Leu Met Lys Tyr Leu Gly Asn Ala Thr Ala Ile Phe Phe Leu Pro Asp
                245                 250                 255

Glu Gly Lys Leu Gln His Leu Glu Asn Glu Leu Thr His Asp Ile Ile
            260                 265                 270

Thr Lys Phe Leu Glu Asn Glu Asp Arg Arg Ser Ala Ser Leu His Leu
        275                 280                 285

Pro Lys Leu Ser Ile Thr Gly Thr Tyr Asp Leu Lys Ser Val Leu Gly
    290                 295                 300

Gln Leu Gly Ile Thr Lys Val Phe Ser Asn Gly Ala Asp Leu Ser Gly
305                 310                 315                 320

Val Thr Glu Glu Ala Pro Leu Lys Leu Ser Lys Ala Val His Lys Ala
                325                 330                 335

Val Leu Thr Ile Asp Glu Lys Gly Thr Glu Ala Ala Gly Ala Met Phe
            340                 345                 350

Leu Glu Ala Ile Pro Met Ser Ile Pro Pro Lys Val Lys Phe Asn Lys
        355                 360                 365

Pro Phe Val Phe Leu Met Ile Glu Gln Asn Thr Lys Ser Pro Leu Phe
    370                 375                 380

Met Gly Lys Val Val Asn Pro Thr Gln Lys
385                 390

<210> SEQ ID NO 8
<211> LENGTH: 394
<212> TYPE: PRT
<213> ORGANISM: Homo sapiens

<400> SEQUENCE: 8

Glu Asp Pro Gln Gly Asp Ala Ala Gln Lys Thr Asp Thr Ser His His
1               5                   10                  15

Asp Gln Asp His Pro Thr Phe Asn Lys Ile Thr Pro Asn Leu Ala Glu
            20                  25                  30

Phe Ala Phe Ser Leu Tyr Arg Gln Leu Ala His Gln Ser Asn Ser Thr
        35                  40                  45

Asn Ile Phe Phe Ser Pro Val Ser Ile Ala Thr Ala Phe Ala Met Leu
    50                  55                  60

Ser Leu Gly Thr Lys Ala Asp Thr His Asp Glu Ile Leu Glu Gly Leu
65                  70                  75                  80

Asn Phe Asn Leu Thr Glu Ile Pro Glu Ala Gln Ile His Glu Gly Phe
```

```
                        85                  90                  95
Gln Glu Leu Leu Arg Thr Leu Asn Gln Pro Asp Ser Gln Leu Gln Leu
            100                 105                 110

Thr Thr Gly Asn Gly Leu Phe Leu Ser Glu Gly Leu Lys Leu Val Asp
        115                 120                 125

Lys Phe Leu Glu Asp Val Lys Leu Tyr His Ser Glu Ala Phe Thr
    130                 135                 140

Val Asn Phe Gly Asp Thr Glu Glu Ala Lys Lys Gln Ile Asn Asp Tyr
145                 150                 155                 160

Val Glu Lys Gly Thr Gln Gly Lys Ile Val Asp Leu Val Lys Glu Leu
                165                 170                 175

Asp Arg Asp Thr Val Phe Ala Leu Val Asn Tyr Ile Phe Phe Lys Gly
            180                 185                 190

Lys Trp Glu Arg Pro Phe Glu Val Lys Asp Thr Glu Glu Asp Phe
        195                 200                 205

His Val Asp Gln Val Thr Thr Val Lys Val Pro Met Met Lys Arg Leu
    210                 215                 220

Gly Met Phe Asn Ile Gln His Cys Lys Lys Leu Ser Ser Trp Val Leu
225                 230                 235                 240

Leu Met Lys Tyr Leu Gly Asn Ala Thr Ala Ile Phe Phe Leu Pro Asp
                245                 250                 255

Glu Gly Lys Leu Gln His Leu Glu Asn Glu Leu Thr His Asp Ile Ile
            260                 265                 270

Thr Lys Phe Leu Glu Asn Glu Asp Arg Arg Ser Ala Ser Leu His Leu
        275                 280                 285

Pro Lys Leu Ser Ile Thr Gly Thr Tyr Asp Leu Lys Ser Val Leu Gly
    290                 295                 300

Gln Leu Gly Ile Thr Lys Val Phe Ser Asn Gly Ala Asp Leu Ser Gly
305                 310                 315                 320

Val Thr Glu Glu Ala Pro Leu Lys Leu Ser Lys Ala Val His Lys Ala
                325                 330                 335

Val Leu Thr Ile Asp Glu Lys Gly Thr Glu Ala Ala Gly Ala Met Phe
            340                 345                 350

Leu Glu Ala Ile Pro Met Ser Ile Pro Pro Glu Val Lys Phe Asn Lys
        355                 360                 365

Pro Phe Val Phe Leu Met Ile Asn Gln Asn Thr Lys Ser Pro Leu Phe
    370                 375                 380

Met Gly Lys Val Val Asn Pro Thr Gln Lys
385                 390

<210> SEQ ID NO 9
<211> LENGTH: 27
<212> TYPE: DNA
<213> ORGANISM: Artificial Sequence
<220> FEATURE:
<223> OTHER INFORMATION: Oligonucleotide for site specific mutation1

<400> SEQUENCE: 9
actcaagggt gtattgtgga tttggtc                                        27

<210> SEQ ID NO 10
<211> LENGTH: 30
<212> TYPE: DNA
<213> ORGANISM: Artificial Sequence
<220> FEATURE:
<223> OTHER INFORMATION: Oligonucleotide for site specific mutation2

<400> SEQUENCE: 10
```

```
aattacatct gctttaaatg ggagagaccc                                         30
```

<210> SEQ ID NO 11
<211> LENGTH: 27
<212> TYPE: DNA
<213> ORGANISM: Artificial Sequence
<220> FEATURE:
<223> OTHER INFORMATION: Oligonucleotide for site specific mutation3

<400> SEQUENCE: 11

```
atccagcact ctaagaagct gtccagc                                            27
```

<210> SEQ ID NO 12
<211> LENGTH: 394
<212> TYPE: PRT
<213> ORGANISM: Homo sapiens

<400> SEQUENCE: 12

```
Glu Asp Pro Gln Gly Asp Ala Ala Gln Lys Thr Asp Thr Ser His His
 1               5                  10                  15

Asp Gln Asp His Pro Thr Phe Asn Lys Ile Thr Pro Asn Leu Ala Glu
            20                  25                  30

Phe Ala Phe Ser Leu Tyr Arg Gln Leu Ala His Gln Ser Asn Ser Thr
        35                  40                  45

Asn Ile Phe Phe Ser Pro Val Ser Ile Ala Thr Ala Phe Ala Met Leu
    50                  55                  60

Ser Leu Gly Thr Lys Ala Asp Thr His Asp Glu Ile Leu Glu Gly Leu
65                  70                  75                  80

Asn Phe Asn Leu Thr Glu Ile Pro Glu Ala Gln Ile His Glu Gly Phe
                85                  90                  95

Gln Glu Leu Leu Arg Thr Leu Asn Gln Pro Asp Ser Gln Leu Gln Leu
            100                 105                 110

Thr Thr Gly Asn Gly Leu Phe Leu Ser Glu Gly Leu Lys Leu Val Asp
        115                 120                 125

Lys Phe Leu Glu Asp Val Lys Lys Leu Tyr His Ser Glu Ala Phe Thr
    130                 135                 140

Val Asn Phe Gly Asp Thr Glu Glu Ala Lys Lys Gln Ile Asn Asp Tyr
145                 150                 155                 160

Val Glu Lys Gly Thr Gln Gly Cys Ile Val Asp Leu Val Lys Glu Leu
                165                 170                 175

Asp Arg Asp Thr Val Phe Ala Leu Val Asn Tyr Ile Cys Phe Lys Gly
            180                 185                 190

Lys Trp Glu Arg Pro Phe Glu Val Lys Asp Thr Glu Glu Asp Phe
        195                 200                 205

His Val Asp Gln Val Thr Thr Val Lys Val Pro Met Met Lys Arg Leu
    210                 215                 220

Gly Met Phe Asn Ile Gln His Cys Lys Lys Leu Ser Ser Trp Val Leu
225                 230                 235                 240

Leu Met Lys Tyr Leu Gly Asn Ala Thr Ala Ile Phe Phe Leu Pro Asp
                245                 250                 255

Glu Gly Lys Leu Gln His Leu Glu Asn Glu Leu Thr His Asp Ile Ile
            260                 265                 270

Thr Lys Phe Leu Glu Asn Glu Asp Arg Arg Ser Ala Ser Leu His Leu
        275                 280                 285

Pro Lys Leu Ser Ile Thr Gly Thr Tyr Asp Leu Lys Ser Val Leu Gly
    290                 295                 300
```

Gln Leu Gly Ile Thr Lys Val Phe Ser Asn Gly Ala Asp Leu Ser Gly
305                 310                 315                 320

Val Thr Glu Glu Ala Pro Leu Lys Leu Ser Lys Ala Val His Lys Ala
                325                 330                 335

Val Leu Thr Ile Asp Glu Lys Gly Thr Glu Ala Ala Gly Ala Met Phe
            340                 345                 350

Leu Glu Ala Ile Pro Met Ser Ile Pro Pro Glu Val Lys Phe Asn Lys
        355                 360                 365

Pro Phe Val Phe Leu Met Ile Glu Gln Asn Thr Lys Ser Pro Leu Phe
    370                 375                 380

Met Gly Lys Val Val Asn Pro Thr Gln Lys
385                 390

<210> SEQ ID NO 13
<211> LENGTH: 394
<212> TYPE: PRT
<213> ORGANISM: Homo sapiens

<400> SEQUENCE: 13

Glu Asp Pro Gln Gly Asp Ala Ala Gln Lys Thr Asp Thr Ser His His
1               5                   10                  15

Asp Gln Asp His Pro Thr Phe Asn Lys Ile Thr Pro Asn Leu Ala Glu
            20                  25                  30

Phe Ala Phe Ser Leu Tyr Arg Gln Leu Ala His Gln Ser Asn Ser Thr
        35                  40                  45

Asn Ile Phe Phe Ser Pro Val Ser Ile Ala Thr Ala Phe Ala Met Leu
    50                  55                  60

Ser Leu Gly Thr Lys Ala Asp Thr His Asp Glu Ile Leu Glu Gly Leu
65                  70                  75                  80

Asn Phe Asn Leu Thr Glu Ile Pro Glu Ala Gln Ile His Glu Gly Phe
                85                  90                  95

Gln Glu Leu Leu Arg Thr Leu Asn Gln Pro Asp Ser Gln Leu Gln Leu
            100                 105                 110

Thr Thr Gly Asn Gly Leu Phe Leu Ser Glu Gly Leu Lys Leu Val Asp
        115                 120                 125

Lys Phe Leu Glu Asp Val Lys Lys Leu Tyr His Ser Glu Ala Phe Thr
130                 135                 140

Val Asn Phe Gly Asp Thr Glu Glu Ala Lys Lys Gln Ile Asn Asp Tyr
145                 150                 155                 160

Val Glu Lys Gly Thr Gln Gly Cys Ile Val Asp Leu Val Lys Glu Leu
                165                 170                 175

Asp Arg Asp Thr Val Phe Ala Leu Val Asn Tyr Ile Cys Phe Lys Gly
            180                 185                 190

Lys Trp Glu Arg Pro Phe Glu Val Lys Asp Thr Glu Glu Glu Asp Phe
        195                 200                 205

His Val Asp Gln Val Thr Thr Val Lys Val Pro Met Met Lys Arg Leu
    210                 215                 220

Gly Met Phe Asn Ile Gln His Ser Lys Lys Leu Ser Ser Trp Val Leu
225                 230                 235                 240

Leu Met Lys Tyr Leu Gly Asn Ala Thr Ala Ile Phe Phe Leu Pro Asp
                245                 250                 255

Glu Gly Lys Leu Gln His Leu Glu Asn Glu Leu Thr His Asp Ile Ile
            260                 265                 270

Thr Lys Phe Leu Glu Asn Glu Asp Arg Arg Ser Ala Ser Leu His Leu
        275                 280                 285

```
                            -continued
Pro Lys Leu Ser Ile Thr Gly Thr Tyr Asp Leu Lys Ser Val Leu Gly
    290             295             300
Gln Leu Gly Ile Thr Lys Val Phe Ser Asn Gly Ala Asp Leu Ser Gly
305             310             315                         320
Val Thr Glu Glu Ala Pro Leu Lys Leu Ser Lys Ala Val His Lys Ala
            325                 330             335
Val Leu Thr Ile Asp Glu Lys Gly Thr Glu Ala Ala Gly Ala Met Phe
            340             345                 350
Leu Glu Ala Ile Pro Met Ser Ile Pro Pro Glu Val Lys Phe Asn Lys
        355             360                 365
Pro Phe Val Phe Leu Met Ile Glu Gln Asn Thr Lys Ser Pro Leu Phe
    370             375             380
Met Gly Lys Val Val Asn Pro Thr Gln Lys
385             390
```